United States Patent [19]

Harvey

[11] 4,182,915
[45] Jan. 8, 1980

[54] PREPARATION OF SUBSTITUTED AROMATIC COMPOUNDS

[75] Inventor: Robert J. Harvey, Teaneck, N.J.

[73] Assignee: Halcon International, Inc., New York, N.Y.

[21] Appl. No.: 762,068

[22] Filed: Jan. 24, 1977

[51] Int. Cl.$^2$ .............. C07C 39/02; C07C 39/12; C07D 307/00
[52] U.S. Cl. .................... 568/716; 260/781; 260/346.11; 568/732; 568/735; 568/744
[58] Field of Search ............ 260/621 R, 578, 581, 260/346.11, 346.22; 568/716, 735, 732, 744

[56] References Cited

PUBLICATIONS

McKilop et al., "Advances in Organometallic Chemistry", vol. 11, pp. 147-201, esp. pp. 169-177.
Taylor et al., "J. Org. Chem.", vol. 40, No. 16, 1975, pp. 2351-2355.
Taylor et al., "JACS", 92:7, Apr. 8, 1970, pp. 2175-2177.
Taylor et al., "JACS", 92:11, Jun. 3, 1970, pp. 3520-3522.

*Primary Examiner*—Werren B. Lone
*Attorney, Agent, or Firm*—William C. Long; David Dick; Jack B. Murray, Jr.

[57] ABSTRACT

Process for the preparation of nucleophilically ring-substituted aromatic compounds from an aromatic-thallium (III) metallate is provided in which the aromatic-thallium (III) metallate is contacted with a source of the nucleophile to form the desired substituted aromatic compound, which may be recovered from the reaction mixture as by distillation. Exemplary processes include the preparation of aniline and phenol from benzene.

16 Claims, No Drawings

PREPARATION OF SUBSTITUTED AROMATIC COMPOUNDS

BACKGROUND OF THE INVENTION

1. Field of the Invention

This invention relates generally to the preparation of nucleophilically ring-substituted aromatic compounds, and more specifically to the preparation of such aromatic compounds by the reaction of aromatic-thallium (III) metallates with a source of the nucleophilic substituent.

2. Description of the Prior Art

It is known that aromatic compounds undergo metallation when reacted with a thallium (III) salt, resulting in the formation of an unsaturated organometallic compound (hereinafter referred to as "aromatic-thallium (III) metallate") through replacement of a carbon-hydrogen bond by a carbon-thallium (III) bond. An example of such a metallation reaction, the thallation of benzene, may be illustrated by the following equation (1):

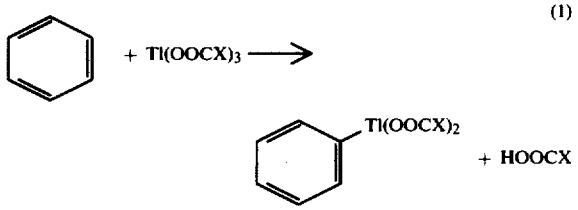

wherein X is an organic radical, such as for example $CH_3$, $CH(CH_3)_2$ or $CF_3$.

These metallates have been employed to obtain such aromatic derivatives as (1) aryl iodides by reaction with aqueous potassium iodide (E. C. Taylor et al., 92(7) *J. Amer. Chem. Soc.* 2176 (1970) ("Taylor I"); A. McKillop et al., *Tetrehedron Letters*, 2427 (1969) ("McKillop I"); E. C. Taylor et al. 3 *Accts. Chem. Res.* 338 (1970) ("Taylor II"); E. C. Taylor et al., 93 (19) *J. Amer. Chem. Soc.* 4841 (1971) (Taylor III"); E. C. Taylor et al, 93 (19) *J. Amer. Chem. Soc.* 4845 (1971) ("Taylor IV")); (2) aryl nitrates by reaction with $NO_2$ (Davies, et al., *J. Chem. Soc. Perkins I*, 65 (1975)); (3) nitro aryl iodides by successive reactions with acetyl nitrate and iodine (E. C. Taylor et al., 40 *J. Org. Chem.* 3441 (1975)); and (4) nitro aryls by reaction of dichlorothallium (III) aryl metallate with nitrosyl chloride (E. C. Taylor et al., 38 *J. Org. Chem.* 2088 (1973)).

Also, aromatic-thallium (III) metallates have been used in the preparation of aryl alcohols by reaction of the metallate with lead tetraacetate, followed by addition of triphenyl phosphine to the reaction mixture and hydrolysis of the resulting intermediate with aqueous base. (Taylor II supra at pages 344-345; and E. C. Taylor et al., 92(11) *J. Amer. Chem. Soc.* 3520 (1970) ("Taylor V")). Deuterated aryls have also been formed by reaction of the metallate with lithium aluminum deuteride or by reduction with aluminum amalgam in $D_2O$ (Taylor et al. II supra at page 345 and M. J. Zelesko, Ph. D. Thesis, Princeton University (1970)).

Bisaryl thallium compounds (which are formed by refluxing aromatic-thallium (III) metallate in acetone followed by addition of water to the reaction mixture) have also been treated by similar methods to obtain aryl iodides and aryl alcohols. Thus, such bisaryl thallium compounds have been reacted with excess $I_2$ in $CHCl_3$ to form iodides and with lead tetraacetate/triphenyl phosphine/aqueous base to form aryl alcohols. See E. C. Taylor et al. 40 (16) *J. Org. Chem.* 2351 (1975) ("Taylor VI").

However, a broader application of metallates in the synthesis of substituted aromatic compounds has been heretofore believed to require photolysis to initiate a free radical reaction involving Ar radicals, in which "Ar" represents the aryl moiety. Thus, aryl thiocyanates and aryl cyanides have been formed by reaction of an aromatic-thallium (III) metallate with KSCN and KCN, respectively, with photolysis required of the reaction mixture to form the desired substituted aromatic compound. (See E. C. Taylor et al, Synthesis 38 (1971) as to the aryl thiocyanates and Taylor II supra and Taylor V, supra as to the aryl cyanides). Likewise, aryl thiophenols have been formed by stepwise reaction of an aromatic-thallium (III) metallate with

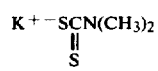

and water, followed by photolysis of the resulting intermediate (Taylor II, supra at pages 343-344), and aniline has been reportedly formed by photolysis of phenyl ditrifluoroacetato thallium in the presence of ammonia (Taylor II, supra at page 344). Finally, bisaryls (such as biphenyl) have been formed from the bisaryl thallium compounds of Taylor VI, supra, by photolysis of the latter thallium compounds in the presence of benzene.[*]

[*]See also E. C. Taylor, et al., 92 (20) *J. Amer. Chem. Soc.* 6088 (1970)-bisaryls via photolysis of arylthallium ditrifluoroacetates in benzene.

While it has been suggested to use the reaction of aryl thallium dicarboxylates and nitrosyl chloride (in which aryl nitroso compounds are formed) to introduce amino functionalities into aromatic nuclei (See, e.g., A. McKillop and E. C. Taylor, *Advances in Organometallic Chemistry*, vol. 11, 147, 170-171 (1973) ("McKillop II")), such reactions are not readily adaptable to direct amination of aromatic-thallium (III) metallates, and conversion of aryl nitroso compounds to the corresponding aryl amines requires increased processing time and equipment.

SUMMARY OF THE INVENTION

According to the present invention a process for the production of nucleophically ring-substituted aromatic compounds is provided which comprises contacting an aromatic-thallium (III) metallate with a source of the nucleophilic substituent to produce the desired substituted aromatic compound. It has been surprisingly found that thallium (III) may be displaced from the aromatic ring of an aromatic-thallium (III) metallate by reacting the metallate with a nucleophile source in an essentially non-photolytic manner, thereby avoiding the generation of substantial quantities of free radical, as is shown by the absence of significant quantities of bisaryl compounds (e.g., biphenyl) in product mixtures obtained by the process of this invention. Also encompassed herein are processes for producing aniline and/or phenol from benzene via intermediate formation of an appropriate aromatic-thallium (III) metallate.

DETAILED DESCRIPTION OF THE INVENTION

According to the process of the present invention, aromatic-thallium (III) metallate of the aromatic compound on which nucleophilic substitution is desired, is reacted (preferably in aqueous or non-aqueous liquid medium) with a source of the selected nucleophile to form the corresponding nucleophilically ring-substituted aromatic compound.

The term "nucleophilic substituent" is intended to refer to negatively charged ions having at least one unshared pair of electrons capable of displacing a thallium group from the nucleus of an aromatic compound. As used herein, the term "nucleophile source" is intended to refer to those nucleophilic reagents which contain at least one such nucleophilic substituent or which function as a source of such nucleophile in the reaction zone under reaction conditions. Since aryl iodides and aryl bromides have been previously produced by the art from aromatic-thallium (III) metallates (see, e.g., McKillop II, supra, page 164), I⁻ and Br⁻ are expressly excluded from the definition of the term "nucleophilic substituent."

Exemplary of nucleophilic substituents useful in the present invention are members selected from the group consisting of —OH, —CN, —OCN, —SCN, —NH₂, —NRR', —NHR, —SH, —SR, —OR, —Cl, —F, —HCO₃,

and mixtures thereof, wherein R and R' are the same or different and are each organic moieties and are preferably members independently selected from the group consisting of alkyl, nitroaryl, aryl, cycloalkyl, aralkyl, alkaryl and heterocyclic. When either "R" or "R'" is alkyl, the alkyl group can be branched or straight-chained and generally contains from 1 to 12 carbon atoms, and preferably contains from 1 to 6 carbon atoms. Examples of such alkyl groups are methyl, ethyl, isopropyl, pentyl, octyl and dodecyl. When either "R" or "R'" is cycloalkyl, the cycloalkyl group generally contains from 3 to 12 carbon atoms, and preferably contains from 4 to 8 carbon atoms. Examples of such groups are cyclopropyl, cyclobutyl, cyclohexyl, cyclooctyl and cyclododecyl. When either "R" or "R'" is alkaryl, the aryl component generally consists of phenyl or tolyl and the alkyl component generally has from 1 to 12 carbon atoms, and preferably from 1 to 6 carbon atoms. Examples of such alkaryl groups are tolyl, m-ethylphenyl, o-ethyltolyl and m-hexyltolyl. When "R" or "R'" is aralkyl, the aralkyl group generally consists of phenyl or alkyl-substituted phenyl as the aryl component and an alkyl component having from 1 to 12 carbon atoms and preferably from 1 to 6 carbon atoms. Examples of such aralkyl groups are benzyl, o-ethylbenzyl and 4-isobutyl benzyl. When either 37 R" or "R'" is aryl or nitroaryl, the aryl group is generally phenyl.

When either "R" or "R'" is heterocyclic, the heterocyclic group generally consists of a compound having at least one ring of 6 to 12 members in which one or more ring carbon atoms is replaced by oxygen or nitrogen. Examples of such heterocyclic groups are furyl, pyranyl, pyridyl, piperidyl, dioxanyl, tetrahydrofuryl, pyrazinyl and 1,4-oxazinyl.

The selected nucleophilic substituent is supplied to the reaction zone as a source of a nucleophile, which is preferably soluble in the selected liquid medium, where a liquid is employed in the reaction zone. When the selected nucleophilic substituent to be introduced to the aromatic compound is hydroxy (—OH), the source of this nucleophile will generally comprise a member selected from the group consisting of water, alkali metal hydroxides, alkaline earth metal hydroxides, ammonium hydroxide, quaternary ammonium hydroxides, and mixtures thereof. Exemplary of alkali metal and alkaline earth metal hydroxides are potassium hydroxide, sodium hydroxide, lithium hydroxide, calcium hydroxide, barium hydroxide and magnesium hydroxide. When the selected nucleophilic substituent comprises cyanide (—CN), the source of the cyanide group will generally comprise a member selected from the group consisting of alkali metal cyanides, alkaline earth metal cyanides, ammonium cyanide, quaternary ammonium cyanides and mixtures thereof. Exemplary of such sources of cyanide are sodium, potassium, lithium, barium and magnesium cyanides. When the selected nucleophilic substituent comprises cyanato (—OCN), the source of the cyanato group will generally comprise a member selected from the group consisting of ammonium cyanate, alkali metal cyanates, alkaline earth metal cyanates, quaternary ammonium cyanates and mixtures thereof. When the selected nucleophilic substituent comprises thiocyanato (—SCN), the source of the thiocyanate group will generally comprise a member selected from the group consisting of ammonium thiocyanate, alkali metal thiocyanates, alkaline earth metal thiocyanates, quaternary ammonium thiocyanates and mixtures thereof. When the selected nucleophilic substituent is —OR, wherein "R" is as defined above, the source of such ether groups will generally comprise a member selected from the group consisting of alcohols having the formula ROH, wherein "R" is as defined above, alkali metal and alkaline earth metal salts of such alcohols and mixtures thereof. Examples of such sources of ether nucleophiles are the alkanols of 1 to 12 carbon atoms, preferably of 1 to 6 carbon atoms (such as methanol, ethanol, isopropanol, isobutanol and 2-hexanol), phenol, benzyl alcohol, m-tolyl alcohol, m-ethyl phenol, 2-ethyl-3-methyl-hydroxy toluene, 3-hexyl-5-methyl-hydroxy toluene, cyclohexanol, 3-hydroxy pyridine and 2-hydroxy furan and alkali metal and alkaline earth metal salts of the foregoing, such as sodium methoxide, potassium ethoxide, sodium phenoxide and potassium benzoxide.

When the selected nucleophilic substituent is —SR, wherein "R" is as defined above, the source of the —SR group will generally comprise a member selected from the group consisting of mercaptans having the formula RSH, wherein "R" is as defined above and alkali metal, alkaline earth metal, ammonium and quaternary ammonium salts thereof. Exemplary of such mercaptans are methyl mercaptan, ethyl mercaptan, and ammonium, sodium and potassium salts thereof. When the selected nucleophilic substituent is —SH, the source of this nucleophile will generally comprise a member selected from the group consisting of quaternary ammonium hydrosulfides, ammonium hydrosulfide, alkali metal hydrosulfides, alkaline earth metal hydrosulfides and mixtures thereof. Exemplary of such sources of —SH are tetramethyl ammonium hydrosulfide, tetraethyl ammonium hydrosulfide, sodium hydrosulfide, potassium hydrosulfide and calcium hydrosulfide. When either fluoro or chloro is the selected nucleophilic substituent, the source of such nucleophile will generally comprise a member selected from the group consisting of ammonium fluoride or chloride, alkali metal and alkaline earth metal fluorides or chlorides, quaternary ammonium fluorides or chlorides, or fluorides or chlorides of transition metals (e.g., copper). Exemplary of such sources of fluoro and chloro are sodium chloride, potassium chloride, sodium fluoride and potassium fluoride.

When —$NH_2$ is the selected nucleophilic substituent, the nucleophile source will generally comprise a member selected from the group consisting of ammonia, compounds which liberate $NH_3$ in basic aqueous media and mixtures thereof. Exemplary compounds which liberate $NH_3$ in basic aqueous media are compounds containing $NH_4^+$ ion, such as ammonium hydroxide and ammonium halide (e.g., ammonium iodide, ammonium fluoride, ammonium bromide and ammonium chloride). Ammonia can be employed as a gas or liquid. Where gaseous ammonia is used, any gas containing $NH_3$ may be employed. The nucleophile source is preferably ammonia, either alone or in combination with other sources of —$NH_2$, when a non-aqueous liquid medium is employed, in order to provide increased conversions to the desired aromatic amine.

When —NHR or —NRR' is the selected nucleophilic substituent, the nucleophile source will comprise the corresponding primary or secondary amine having the formula $NH_2R$ and

respectively, wherein "R" and "R'" are as defined above. Examples of such primary amine nucleophile sources are $NH_2CH_3$, $NH_2CH_2CH_3$, aniline, isobutyl amine, and cyclohexylamine. Examples of such secondary amine nucleophile sources are methyl ethylamine, di-n-butylamine, diphenylamine, dicyclopentyl amine, and dibenzyl amine.

When

is the selected nucleophilic substituent, the nucleophile source will comprise the corresponding carboxylic acid having the formula

wherein "R" is as defined above. Examples of such nucleophile sources are acetic acid, benzoic acid, propionic acid, toluic acid, p-nitrobenzoic acid, butyric acid and isobutric acid.

As will be apparent from the foregoing, so long as the compound chosen as the nucleophile source functions in the reaction zone under reaction conditions to provide the selected nucleophilic substituent which is to be substituted on the aromatic ring of the aromatic-thallium (III) metallate, there is no criticality as to selection of the nucleophile source.

The aromatic-thallium (III) metallates which can be employed as starting material in the process of the present invention comprise organic compounds containing at least one aromatic ring on which is substituted a thallic group having the formula:

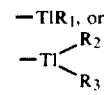

wherein Tl is trivalent thallium, $R_1$ is —$CO_3$ or —$SO_4$, and $R_2$ and $R_3$ are the same or different and are members selected from the group consisting of

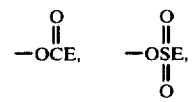

—$NO_3$, and halide, wherein E is a member selected from the group consisting of (i) alkyl, (ii) cycloalkyl, (iii) alkaryl, (iv) aralkyl, (v) aryl, (vi) derivatives of the above hydrocarbyl groups wherein at least one carbon atom is replaced by oxygen, (vii) derivatives of the above hydrocarbyl and oxygen-substituted hydrocarbyl groups in which at least one hydrogen atom is replaced by a member selected from the group consisting of —$NO_2$, —OH and alkoxy, and (viii) halogenated derivatives of the foregoing; and mixtures of the above metallates. As used herein, the term "thallic" refers to trivalent thallium, i.e. "thallium (III)", and the term "thallous" refers to monovalent thallium, i.e., "thallium (I)."

When "E" is alkyl, the alkyl group can be branched or straight-chained and generally contains from 1 to 12 carbon atoms, and preferably contains from 1 to 6 carbon atoms. Examples of such alkyl groups are methyl, ethyl, isopropyl, isobutyl, pentyl, octyl and dodecyl. When "E" is cycloalkyl, the cycloalkyl group generally contains from 3 to 12 carbon atoms and preferably contains from 4 to 8 carbon atoms. Examples of such groups are cyclopropyl, cyclobutyl, cyclohexyl, cyclooctyl and cyclododecyl. When "E" is alkaryl, the aryl component generally consists of phenyl or tolyl and the alkyl component generally has from 1 to 12 carbon atoms and preferably from 1 to 6 carbon atoms. Examples of such alkaryl groups are tolyl, m-ethylphenyl, o-ethyltolyl and m-hexyltolyl. When "E" is aralkyl, the aralkyl group generally consists of phenyl or alkyl-substituted phenyl as the aryl component and an alkyl component having from 1 to 12 carbon atoms and benzyl, o-ethylbenzyl and 4-isobutyl benzyl. When "E" is aryl, the aryl group is generally phenyl.

As indicated above, "E" may also comprise alkyl, cycloalkyl, alkaryl aralkyl or aryl in which at least one carbon atom is replaced by an oxygen atom. Such "E" groups therefore include (i) straight-chained alkyl ether groups having the formula —$(CH_2)_{m_1}O(CH_2)_{m_2}CH_3$, wherein $m_1$ is an integer of 1 to 10, $m_2$ is an integer of 0 to 9, and $m_1 + m_2$ is from 1 to 11 (e.g., methoxy methyl, ethoxy ethyl, propoxy octyl and heptoxy butyl); (2) branched-chain alkyl ether groups of 4 to 11 carbon atoms, such as isopropoxy methyl, isobutoxy decyl, methoxy isobutyl and isopropoxy pentyl; (3) aralkyl ether groups having the formula $AO(CH_3)_2$- or $A(CH_2)_{t_1}O(CH_2)_{t_2}$-, wherein A is the aryl component and generally comprises phenyl or alkyl-substituted phenyl, s is an integer of 1 to 10, $t_1$ is an integer of 1 to 10, and t₂ is an integer of 1 to 10, and derivatives of the above in which at least one hydrogen in the alkyl component is replaced by alkyl of 1 to 6 carbon atoms (e.g., p-methylphenoxy heptyl, 5-phenyl-1-methylpentoxy propyl, phenoxy ethyl and phenoxy isopropyl); (4) alkaryl ether groups wherein the alkyl component can be either a branched-chain alkyl ether group of 4 to 11 carbon atoms or a straight-chained alkyl ether group having the formula —(CH₂)$_{n1}$O(CH₂)$_{n2}$CH₃, in which n₁ is an integer of 0 to 10, and n₂ is an integer of 0 to 10, and wherein the aryl component is generally phenyl or tolyl (e.g., m-methoxy phenyl, isopropoxy phenyl, 2-methyl-4-(butoxy ethyl) phenyl and p-(isopropoxy butyl)-phenyl); and (5) cyclic ether groups such as furyl and tetrahydrofuryl and monovalent radicals derived from 1,3- and 1,4-dioxane.

Exemplary of "E" as nitro, hydroxy or alkoxy derivatives of the foregoing groups are hydroxy methyl, 2-nitro-3-ethoxy propyl, 9-(4-nitro-phenyl)-octyl, 4-nitrophenyl, 2-isopropyl-6-nitro-phenyl, 2-nitro-6-isobutoxy phenyl, 2,4-dinitro phenyl, 2,4-dinitro-3-ethoxy phenyl, 3-methyl-6-hydroxy phenyl, dinitromethyl, 2,4-diethyl butyl, 4-hydroxy phenyl, 3-pentoxy-cyclohexyl, 4-nitrocyclohexyl and 3-hydroxy-5-methoxy cyclooctyl.

When "E" is a halogenated derivative of the foregoing groups, such halogenated groups are radicals in which one or more C—H bonds are substituted by C-Halo bonds in which Halo comprises a member selected from the group consisting of chlorine, fluorine, bromine and iodine. When "E" is a halogenated group, each of radicals R₂ and R₃ may contain halogen substituents of more than one of chlorine, fluorine, bromine and iodine. Exemplary of such halogenated "E" groups are perfluoromethyl, iodomethyl, 2-bromopentyl, 4-chloro-4-methylhexyl, 3-ethoxy-5-iodoheptyl, 1-chloro-8-fluoro-octyl, 3-iodophenyl, 2,6-diiodo-4-methoxyphenyl, 4-(3-iodophenyl)pentyl, 2-fluoro-4-isopropylphenyl, 3-(2-chlorophenoxy)heptyl, 2,4-dinitro-5-bromo-benzyl and 2-hydroxy-3-nitro-4-(4-bromophenoxy)-pentyl.

Thallic groups useful in this invention in which R₁ is —CO₃ or —SO₄ are —TlCO₃ and —TlSO₄. Exemplary of thallic groups useful in this invention in which "R₂" and "R₃" are —NO₃ or halide are —Tl(NO₃)₂, —TlCl₂, —TlBr₂, —TlI₂, —TlF₂, and —Tl(Cl)F.

Preferred as R₂ and R₃ are members independently selected from the group consisting of alkylcarboxylates, arylcarboxylates, alkarylcarboxylates, alkylsulfonates, arylsulfonates, alkarylsulfonates, and halogenated derivatives of the foregoing, wherein the alkyl, aryl, alkaryl, and halogenated derivatives are described above. Examples of especially preferred R₂ and R₃ radicals are:

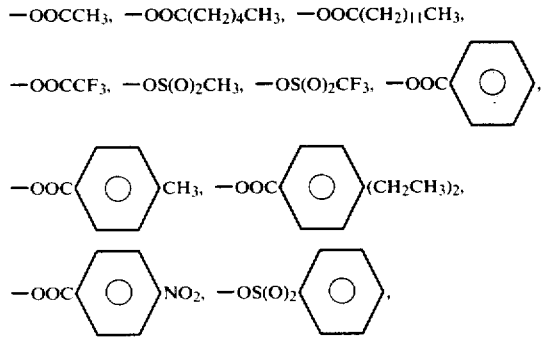

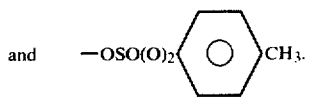

Of the foregoing thallic groups, especially preferred are

moieties wherein R₂ and R₃ are the same and are members selected from the group consisting of —OOCE' in which E' is a member selected from the group consisting of alkyl of 1 to 4 carbon atoms, mononuclear aryl of 6 to 12 carbon atoms, alkaryl of 7 to 10 carbon atoms, aralkyl of 7 to 10 carbon atoms, cycloalkyl of 4 to 8 carbon atoms and halogenated derivatives of the foregoing.

Organic compounds from which aromatic-thallium (III) metallates may be derived for use in the present invention contain at least one aromatic ring, which can be substituted or unsubstituted, and include such aromatic compounds as benzene, naphthalene, anthracene, phenanthrene, mono-, di- or tri-substituted counterparts of any of the above and the like, as well as bisaryl alkyl derivatives of the foregoing, such as bisphenyl alkyls, bisnaphthyl alkyls, bisanthryl alkyls and bisphenanthryl alkyls. Aromatic-thallium (III) metallates may be derived from organic compounds having the formula $(Z_1)_{p1}(Z_2)_{p2}$ wherein p₁ is an integer of 1 to 3; p₂ is an integer of 0 to 3; Z₁ is a radical selected from the group consisting of phenyl, naphthyl, anthryl, phenanthryl, furyl, indenyl, isoindenyl, benzofuryl, and tetrahydrofuryl; and Z₂ is a radical selected from the group consisting of monovalent alkyl, monovalent cycloalkyl, nitro, hydroxy, aryl, alkoxy, alkoxy-substituted alkyl, aryloxy, aralkyl, aliphatic carboxyl, aryl carboxyl, hydroxy-substituted alkyl, alkyl esters, divalent alkyl, halogenated derivatives of the foregoing, and halogen (such as bromo, chloro and fluoro), with the proviso that when Z₂ is a divalent alkyl, p₁ is 2 and p₂ is 1. When p₂ is 2 or 3, the substitutents Z₂ can be the same or different, and can be substituted on the same or different aromatic ring(s). It will be understood that mixtures of the foregoing aromatic compounds and hence, mixtures of different aromatic-thallium (III) metallates, may also be employed.

When "Z₂" is monovalent alkyl, the alkyl group preferably contains from 1 to 6 carbon atoms. Examples of such alkyl groups are methyl, ethyl, propyl, isopropyl, butyl, tert-butyl, amyl, hexyl, cyclohexyl and cyclopentyl. When "Z₂" is aryl, the aryl group generally contains from about 6 to 12 carbon atoms. Exemplary of such aryl groups are phenyl and alkyl-substituted phenyls in which the alkyl substituent(s) contains from 1 to 6 carbon atoms, e.g., tolyl, xylyl, ethylphenyl and isopropyl phenyl. When "Z₂" is monovalent cycloalkyl, the cycloalkyl group generally contains from 3 to 10 carbon atoms. Examples of such cycloalkyl groups are cyclobutyl, cyclopentyl, cyclohexyl, cyclooctyl and cyclodecyl. When "Z₂" is alkoxy, the alkoxy group generally contains from 1 to 6 carbon atoms, and therefore includes such groups as methoxy, ethoxy, propionoxy, butoxy, hexoxy, cyclohexoxy and cyclopentoxy. When "Z₂" is alkoxy-substituted alkyl, the substituted alkyl group generally contains a total of from 2 to 7 carbon atoms. Exemplary of such groups are —CH₂OCH₃, —CH₂CH₂OCH₃ and —(CH₂)₃CH(CH₃)OCH₃. When "Z₂" is aryloxy, the aryloxy group generally contains from 6 to 12 carbon atoms and the aryl substituent will generally comprise phenyl or alkyl-substituted phenyl in which the alkyl substituent contains from 1 to 6 carbon atoms. Examples of such aryloxy groups are phenoxy,

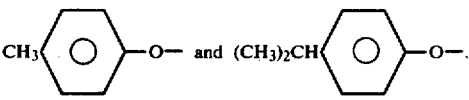

When "Z₂" is aralkyl, the aralkyl group generally contains from 7 to 12 carbon atoms, and the aryl substituent generally comprises phenyl or mono- or dialkyl substituted aryl wherein the alkyl group contains from 1 to 6 carbon atoms. Examples of such aralkyl groups are methylbenzyl, 3-ethylbenzyl, 2,3-dimethylbenzyl and the like. When "Z₂" is divalent alkyl, the divalent alkyl group generally contains from 1 to 12 carbon atoms. Examples of such divalent alkyl groups are —CH₂—, —CH₂CH₂—, —CH₂CH₂CH₂—, —CH₂CH(CH₃)CH₂—, —CH₂CH(CH₂CH₃)CH₂—, and —CH₂CH₂(CH₂)₄CH₂—.

When "Z₂" is aliphatic carboxyl, the aliphatic carboxyl groups generally contain from 1 to 8 carbon atoms, and therefore includes such groups as —COOH, —CH₂COOH, —CH(CH₃)COOH, —C(CH₃)₂COOH, —CH₂CH₂COOH, —CH(CH₃)CH₂COOH and —C(CH₃)₂CH₂COOH. When "Z₂" is alkyl ester, the alkyl ester group generally contains from 2 to 8 carbon atoms, and therefore includes such groups as —COOCH₃, —CH₂CH₂COOCH₃, —CH₂CH₂COOC₂H₅ and —CH₂CH(CH₃)CH₂COOC₂H₅. When "Z₂" is hydroxy-substituted alkyl, the hydroxy substituted alkyl group generally contains from 1 to 6 carbon atoms, and therefore includes such groups as —CH₂OH, —CH₂CH₂OH and —(CH₂)₃CH(CH₃)OH. When "Z₂" is aryl carboxyl, the aryl carboxyl group generally contains from 8 to 12 carbons, and is inclusive of such groups as

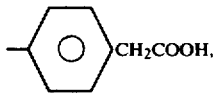 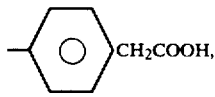

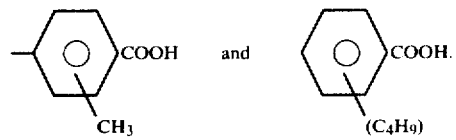

Some more specific aromatic organic compounds from which aromatic-thallic salt metallates may be obtained which may be treated in accordance with the present invention include biphenyl, 4,4'-dichlorobiphenyl, toluene o-, m- and p-xylene, chlorobenzene, fluorobenzene, ethylbenzene, anisole, hexylbenzene, phenyl ether, phenol, dihydroxy benzene, 2-bromo-furan, 2(bromomethyl)furan, 2(tert-butyl)tetrahydrofuran, 2-ethoxy furan, 1,2-diphenylindene, 2,3-dihydra-indene, 3-methoxyisoindene, phenetole, o-, m- and p-xylene, 1-chloronaphthalene, 2,5-dichloronaphthalene, 1-fluoroanthracene, 2-methylphenanthrene, diphenylmethane, 3-xylyl-1-methylbenzene, 2(bisphenyl)propane, 2(chloromethyl)-2,3-dihydrobenzofuran, 1-methyl-3-ethyl benzene, cyclohexyl benzene, 1-hydroxy-3-chlorobenzene, 4-hydroxy-4'-fluorobiphenyl, 1,4-dichloroanthracene, 2,7-dihydroxy phenanthrene, 2-pentoxy-7-hydroxy phenanthrene, 1-(2,3-dimethyl phenyl)naphthalene, 1,4-dichloronaphthalene, methylisopropyl phenanthrene, 9,10-dichloroanthracene, 9,10-dihydroxy anthracene, 2,3-dimethylanthracene, 9-ethylanthracene, 1-benzyl-naphthalene, 1- or 2-chloronaphthalene, any of the dichloroanthracenes, dimethyl anthracenes, naphthalene diols, dichloronaphthalenes, and dimethylnaphthalenes, 1-ethoxynaphthalene, 1- or 2-fluoronaphthalene, isopropylmethyl naphthalene, 1- or 2-ethylnaphthalene, 1-methylisopropylnaphthalene, 1-phenylnaphthalene, and the like as well as any other compounds which come within the definition and formula set out hereinbefore which will occur to those skilled in the art.

Preferred organic compounds from which aromatic-thallium (III) metallates are derived are members selected from the group consisting of benzene, naphthalene, bis-phenyl alkanes, bis-naphthyl alkanes, and alkyl-substituted derivatives of the foregoing in which the alkyl substituent contains from 1 to 6 carbon atoms.

Exemplary of preferred aromatic-thallium (III) metallates useful in the present invention are the following:

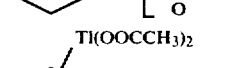
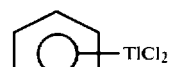
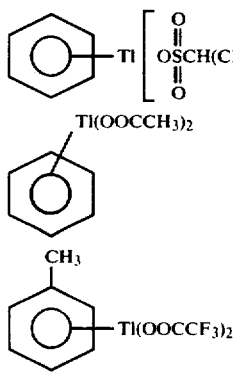
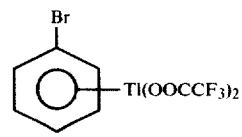

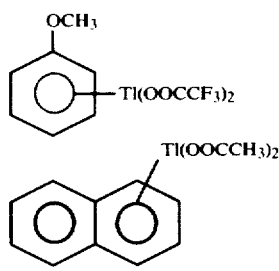
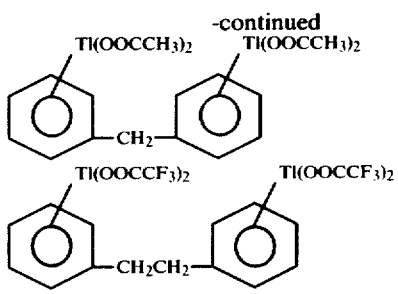

Especially preferred aromatic-thallium (III) metallates treated in accordance with the present invention are phenyl diacetatothallium, phenyl di(trifluoroacetato)thallium, tolyl diacetatothallium and alpha-naphthyl diacetatothallium.

The aromatic-thallium (III) metallate used in the process of the present invention can be obtained by conventional methods, and a detailed discussion of their preparation is not necessary to allow an understanding of the present invention. See, for example, the preparatory procedures described in McKillop II supra, pages 160–163 and the references cited therein, especially J. M. Davidson and C. Triggs. "Reaction of Metal Ion Complexes with Hydrocarbons . . . ", *I. Chem. Soc.* (A) 1324, at 1329 (1968).

In the liquid phase preferred embodiment of the process of the present invention, the selected metallate and source of the nucleophile are contacted in the liquid phase in the reaction zone. The liquid medium selected for use can comprise (1) one or more of the reactants (when a liquid reactant is employed) or (2) a solvent for the selected aromatic-thallium (III) metallate and/or for the nucleophile source. The choice of such solvent will, of course, vary widely and will depend on the type of reactor vessel used, the temperature and pressure selected and other factors. Generally, however, suitable solvents include water, ethers, alcohols, sulfoxides, amides, nitriles and the like, such as tetrahydrofuran, dioxane, dimethylformamide, tert-butanol, methanol, benzene, acetonitrile, dimethylsulfoxide, and the like, with water, methanol, benzene, ethylene glycol diacetate, and tert-butyl alcohol being preferred. The selected solvent is preferably one which does not react adversely with any component of the system to depress yields of the desired product, though the solvent and the nucleophile source (e.g., water) can be identical. The amount of solvent employed is not critical.

While both the aromatic-thallium (III) metallate and nucleophile source will preferably be soluble in the selected liquid media, this is not critical and liquid media in which the metallate, nucleophile source or both are either insoluble or only slightly soluble can also be employed.

The manner of contacting the aromatic-thallium (III) metallate and nucleophile source in the reaction zone is not critical, and the process can be performed in a batchwise, continuous or semi-continuous manner. Thus, a single reaction zone or a plurality of reaction zones in series or parallel can be employed, and the aromatic-thallium (III) metallate and nucleophile source, and solvent or inert liquid (if any) can be fed to the reaction zone separately or as one or more combined stream. As indicated previously, ammonia can be fed to the reaction zone either as a gas or liquid.

The relative amounts of aromatic-thallium (III) metallate and nucleophile source fed to the reaction zone are not critical. However, it is preferable to employ the nucleophile source in an amount in excess of the quantity which is stoichiometrically required to react with the quantity of aromatic-thallium (III) metallate introduced for reaction. Solely for purposes of illustration, the stoichiometry of a typical reaction may be represented by the following equation (2)

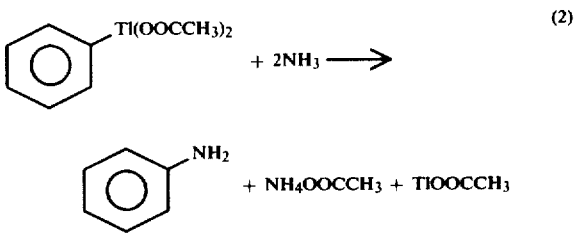

(2)

wherein $NH_3$ is the source of amino nucleophile, and

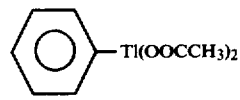

is the aromatic-thallium (III) metallate. Thus, the molar ratio of the nucleophile source to the aromatic-thallium (III) metallate for the above reaction is preferably at least about 2:1.

The process of this invention can be carried out over a wide range of temperatures. Temperatures, for example, from 20° to 500° C. are suitable, with temperatures of from about 50° C. to 300° C. being desired, and temperatures from about 100° to 250° C. being preferred. Temperatures lower than those mentioned can be used but they tend to lead to reduced reaction rates. Higher temperatures than those mentioned can be employed, but there is no particular advantage to such practice.

The process of this invention can also be carried out over a wide range of pressures, with a choice of the pressure being dictated only by economics. In the preferred liquid phase embodiment, the pressure above the liquid phase should be sufficient to maintain at least part of the aromatic-thallium (III) metallate and nucleophile source in the liquid phase. Pressures will normally range from 0.1 to 2000 atmosphere gage, although higher or lower pressures may also be used. For example, while pressures of greater than 2000 atmospheres gage can be used, there is little advantage to their use and a substantial economic penalty would be incurred as a result of the increased cost of equipment capable of withstanding such higher pressures.

Reaction time is not a significant parameter of the process of this invention, depending to a large extent upon the temperature employed as well as upon reactant concentrations. Suitable reaction times (i.e., times sufficient for the aromatic-thallium (III) metallate/nucleophile source reaction to occur) for the liquid phase embodiment will normally be within the range of 0.1 to 100 hours. Reaction time in a batch system is self-explanatory. In a continuous system, the residence time is defined as the quotient obtained by dividing the volume of the liquid phase reaction medium within the reaction zone by the rate (in consistent volume units per hour) at which aromatic-thallium (III) metallate, solvent and nucleophile source (both fresh feed and any recycled material) is introduced to the reaction zone.

Reaction of an aromatic-thallium (III) metallate and a nucleophile source in accordance with the present invention is preferably effected in an essentially non-photolytic manner, that is, the reaction is preferably conducted in the absence of substantial photolysis, e.g., ultra-violet light generated by an ultra-violet light source. The displacement of the thallium group from the aromatic-thallium (III) metallate and the desired nucleophilic substitution on the aromatic ring of the metallate's substrate in accordance with the process of the present invention does not require photolysis, although the reactions to the desired nucleophilically substituted products will proceed (albeit less satisfactorily) in the presence of a photolytic source. However, photolysis is not desired since it can result in undesired formation of by-product bisaryls, such as biphenyl where the metallate is based on phenyl as the aromatic substrate. Therefore, photolysis can sometimes serve to decrease the yield of the desired nucleophilically ring-substituted aromatic compound obtained by the present invention.

It has been found that the process of the present invention can be carried out in the presence of a promoter to achieve higher yields of, and/or higher rates of conversion to, the desired nucleophilically ring-substituted aromatic compound. Suitable promoters in the present invention comprise members selected from the group consisting of iodine sources, copper sources and mixtures thereof. Thus, the promoter can comprise iodine in either the elemental or combined form, copper in either the elemental or combined form, and mixtures thereof. Examples of iodine sources containing combined iodine are compounds containing one or more iodine groups such as iodide ($I^-$), iodate ($IO_3^-$), triiodide ($I_3^-$), hypoiodite ($IO^-$) and periodate ($IO_4^-$). Preferred iodine sources are inorganic salts containing iodine combined with a member selected from the group consisting of hydrogen, ammonium ($NH_4^+$), cations derived from bismuth, copper, iron, cobalt, zinc, nickel, palladium, silver, cadmium, sodium, potassium, or lithium and mixtures thereof, Exemplary iodine sources useful as promoters therefore include: $I_2$, $FeI_3$, $FeI_2$, $ZnI_2$, $CuI$, $CuI_2$, $BiI_3$, $CoI_2$, $AgI$, $NiI_2$, $CdI_2$, $PdI_2$, $MoI$, $KI$, $LiI$, $NaIO_3$, $FeIO_3$, $Ag_2H_3IO_6$, $HI$, $HIO_2$, $HIO_3$, $HIO_4$, $HIO$, $H_2I_2O_6$, $I_2O_4$, $I_2O_9$, $KH(IO_3)_2$, $NH_4H_2(IO_3)_3$, $NaIO_4$, $NaOI$, $Na_2H_3IO_6$, $Na_3H_2IO_6$, $Na_4I_2O_9$ and the like. Mixed halide compounds containing iodine may also be used as promoter in the process of the present invention. Examples of such mixed halides include iodine monochloride and iodine trichloride. Aliphatic organic compounds containing combined iodine (e.g., iodoform, methyliodide, and ethyliodide) may also be employed as a promoter.

Where copper is used as promoter, the copper can be employed in any convenient form, viz., in the zero valent state or in any higher form. For example, metallic copper, preferably in finely divided form, can be added to the reaction zone. Alternatively, the copper source can be added as a carbonate, oxide, hydroxide, nitrate, halide (e.g., as the bromide, iodide, chloride or fluoride), lower alkoxide (e.g., having from 1 to 5 carbon atoms, such as the methoxide or ethoxide), phenoxide, or metal carboxylate (e.g., cupric acetate), wherein the carboxylate ion is derived from an alkanoic acid of 1 to 10 carbon atoms.

As is apparent from the foregoing, there is no criticality with respect to the form in which the promoter is supplied to the system. Any form of iodine and/or copper, including compounds, complexes and the elemental forms themselves can be employed so long as, in the reaction zone under reaction conditions, the form chosen provides a source of either or both of these elements in any valance. Thus, the promoter can comprise a member selected from the group consisting of elemental copper, elemental iodine, compounds or complexes containing copper in any valence state, compounds or complexes containing iodine in any valence state, and mixtures of any of the foregoing.

Preferred as promoters in the practice of the present invention are members selected from the group consisting of iodine salts of iron, cobalt, nickel, copper, zinc, palladium, silver, cadmium, bismuth, ammonium, sodium or potassium; copper in the form of the carbonate, oxide, hydroxide, nitrate, halide, lower alkoxide, phenoxide, or metal carboxylate; elemental iodide; elemental copper; and mixtures thereof.

These promoters are especially useful as amination promoters in forming products of this invention in which $-NH_2$, $-NHR$ or $-NRR'$ (wherein "R" and "R'" are as defined above) is the nucleophile substituent to be introduced to the aromatic ring of the selected metallate, and as hydroxylation promoters in forming products of this invention in which $-OH$ is the nucleophilic substituent to be introduced to the aromatic substrate of the selected aromatic-thallium (III) metallate.

Especially preferred amination promoters are cuprous and cupric chlorides, bromides, iodides, fluorides, and acetates, sodium iodide, zinc iodide, cobalt iodide and cadmium iodide. Especially preferred hydroxylation promoters are cuprous and cupric acetates and iodides.

It will be clear from the foregoing discussion that a single promoter may comprise both an iodide source and a copper source. Examples of such promoters are cuprous iodide, cupric iodide, cuprous iodate, cupric iodate and the like. Likewise, it will be clear from the above discussion, that a single compound can contain the desired nucleophile and a promoter and can thus act as both a nucleophile source and a promoter. An example of the latter class of compounds is ammonium iodide.

For liquid phase reaction systems, the promoter can be employed in forms initially or eventually soluble in the liquid phase reaction medium to provide a homogeneous catalyst system. Alternatively, insoluble (or only partially soluble) forms, providing a heterogeneous promoter system, can be employed. Amounts of promoter (calculated as contained iodine or copper based upon the total quantity of liquid phase reaction medium) of as little as about $1 \times 10^{-4}$ wt. % are effective, although normally amounts of at least 1,000 ppm, desirably at least 10,000 ppm, and preferably at least 20,000 ppm would be employed. Upper concentration limit on promoter quantity in homogeneous systems appear to be controlled more by economics than by any advantage in either rate or selectivity that can be observed. These limits would normally suggest that more than 50,000 ppm of promoter would not normally be employed. An optimum balancing of reaction rate and economic criteria would normally suggest the use of amounts of contained promoter based upon the total weight of liquid phase reaction medium between about 10 and about 50,000 ppm, desirably between about 1,000 and 40,000 ppm, and preferably between about 5,000 and 25,000 ppm.

The zone in which the reaction of the metallate and nucleophile source is effected in accordance with the process of the present invention can comprise one or more autoclaves or an elongated tubular zone or series of such zones. Of course, reaction zone construction should be such that the reaction zone can withstand reaction temperature and pressure and should be fabricated from materials relatively inert to reaction with the components of the reaction mixture. Suitable inert materials for reaction zone construction include titanium, tantalum, zirconium, various stainless steels, the Hastelloys, and the like. The reaction zone is also suitably fitted with appropriate temperature control devices. Suitably, the reaction zone is configured to provide sufficient agitation to insure adequate contact between the reactants. Any convenient agitation means known to those skilled in the art can be used, including vibration, shaking, stirring, etc., as illustrative techniques. A gaseous reactant, such as gaseous ammonia, if employed, would normally be introduced at a point within the reaction zone below the level of the liquid phase reaction medium maintained therewithin in order to facilitate agitation and adequate contact by gas-sparging techniques.

When, —NH$_2$, —NHR or —NRR' (wherein "R" and "R'" are as defined above) is the nucleophile which is to be substituted on the aromatic ring of the aromatic-thallium (III) metallate, the liquid medium is preferably maintained under alkaline conditions throughout the reaction, when the reaction is conducted in the presence of a liquid medium. Use of excess nucleophile source, such as ammonia, ammonium hydroxide or other ammonium compounds for —NH$_2$ nucleophiles and such as amines having the formula NH$_2$ or

for —NHR and —NRR' nucleophiles, respectively, is advantageous in maintaining a liquid reaction medium under alkaline conditions for such amination reactions.

The nucleophilically ring-substituted aromatic compound produced by the process of the present invention can be recovered from a liquid medium by conventional methods. Thus, the liquid medium can be subjected to conventional distillation processes to recover the product aromatic compound therefrom. Unreacted aromatic-thallium (III) metallate and nucleophile source can be recovered from the reaction zone by conventional methods and can be recycled to the process. Likewise, solvent recovered from a liquid medium and promoter (where employed) can be also recycled to the process.

When an aromatic-thallium (III) metallate is reacted with an alkali metal or an alkaline earth metal hydroxide to provide substitution of hydroxy (—OH) nucleophile on the aromatic ring, the alkali metal or alkaline earth metal salt of the hydroxy-substituted aromatic compound is usually formed in the reaction zone and can be hydrolyzed using conventional procedures to liberate the desired aromatic alcohol. Thus, the alkali metal or alkaline earth metal salt of the desired alcohol can be contracted with a suitable acid such as a mineral acid to hydrolyze the salt and form the corresponding alcohol. Suitable mineral acids include hydrochloric acid, hydrobromic acid, sulfuric acid and nitric acid. When the salt to be hydrolyzed is soluble in the liquid medium, the selected mineral acid can be added directly to the liquid and the desired alcohol can be recovered therefrom by conventional distillation. Correspondingly, where the salts to be hydrolyzed are insoluble in the liquid medium present in the reaction zone, the solids can be recovered as by filtration and then contacted with the selected mineral acid to liberate the desired alcohol. Ion-exchange resins can also be employed.

As illustrated in equation (2) above, the reaction of the selected nucleophile source and the selected aromatic-thallium (III) metallate will result in the formation of a thallium (I) salt in addition to the desired aromatic amine. Where desired, the monovalent thallium salt may be recovered from the liquid medium by conventional methods and reoxidized in the trivalent oxidation state. The method by which the monovalent thallium salt is oxidized to the trivalent state is not critical to the present invention and may include any of the conventional methods for oxidizing monovalent thallium, such as those methods described in Gmelin, *Handbuch der Anorganischen Chemie*, 8, pg. 138 (1939); Mellor, *Comprehensive Treatise on Inorganic and Theoretical Chemistry*, vol. 5, Pgs. 406, 420 (Longmans, Green & Co., New York, 1924); and U.S. Pat. No. 3,399,956 (issued to A. Hirose et al.). For example, the monovalent thallium can be oxidized to produce thallic oxide which can be refluxed in aqueous acetic acid to yield thallic acetate which can be recovered in pure form by recrystallization.

Where desired, by-product aromatic compounds formed in the reaction, e.g., iodobenzene formed in the amination of benzene-thallium (III) metallates (such as phenyl diacetato thallium) in the presence of an ammonium halide may be recycled to the process.

From the above discussion it will be appreciated that a mixture of nucleophilically ring-substituted aromatic compounds can be prepared from an aromatic-thallium (III) metallate if the metallate is reacted with a mixture of nucleophile sources containing different nucleophiles. For example, a mixture of phenol and aniline can be obtained by reacting an aromatic-thallium (III) metallate with ammonia in the presence of water. In such an instance, ammonia would comprise a source of —NH$_2$ and the water would comprise a source of —OH. It will be also obvious from the above discussion that a single compound can act as a source of more than one nucleophilic substituent. For example, ammonium hydroxide can result in a product mixture containing both the hydroxy and amino (—NH$_2$) derivative of the metallate with which it is reacted. The choice of the nucleophile source will therefore depend on whether a single nucleophilically ring-substituted aromatic compound, or a mixture of such compounds, is desired.

The invention will be more fully understood by reference to the following specific examples, but it is to be understood that these examples are given solely for illustrative purposes and are not intended to be limiting of the invention. As indicated in the tables below, yields of aniline and phenol are often reported as combined values. In other cases, separate yields of these two products are given.

EXAMPLE 1

To a 30 ml vessel containing 113 mmole of benzene is slowly added 5.5 mmoles of anhydrous thallic triacetate with continuous stirring. The benzene and thallic salt are heated to a temperature of 120° C. at autogenous pressure and allowed to react for a period of 20 hours. After this period, the liquid mixture is stripped to dryness in a thin film evaporator at 45° C. and 0.5 mm Hg liquid is thereby determined by gas chromatography and verified by means of a weighted amount of 4-hydroxy-4-methyl pentanone or a p-xylene/methanol mixture (50 wt. % methanol) added to the samples as an internal standard prior to analysis. Product yields are calculated based on the amount of aromatic-thallium (III) metallate charged and the total weight of product recovered, on the assumption that there is a homogeneous, mechanical interchange of material between the glass insert and the interior of the steel bomb during rotation of the bomb and glass insert in the oil bath during each run. Data thereby obtained is summarized in Table 1 below.

TABLE 1

| Run No. | CHARGE TO REACTOR - MILLIMOLES | | | | PRODUCT YIELD - MOLE % | | |
|---|---|---|---|---|---|---|---|
| | Metallate* | $NH_4I$ | $NH_4OH$ | $NH_3$ | Aniline + Phenol | Phenyl Iodide | Biphenyl |
| 1 | 4.9 | 5.6 | 119 | — | 1.3 | 2.8 | nil |
| 2 | " | 11 | " | — | 1.8 | 3.6 | nil |
| 3 | 9.8 | " | " | — | 3.6 | 1.6 | nil |
| 4 | 2.5 | " | " | — | 0.8 | 5.6 | nil |
| 5 | 4.9 | 2.8 | " | 282 | 1.0 | 6.4 | 4.4 |
| 6 | " | 11.2 | " | 294 | 6.1 | 6.8 | nil |
| 7 | " | 5.6 | " | " | 3.5 | 3.8 | 0.2 |
| 8 | " | " | — | — | 1.5 | 61.6 | 2.8 |

*Metallate is phenyldiacetato thallium, having the formula

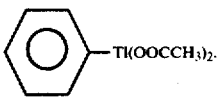

and solid residue is recovered which is analyzed to determine its acetate:thallium ratio and is also subjected to infra-red and NMR analysis, confirming its structure as phenyl diacetatothallium.

EXAMPLE 2

In eight separate runs, selected amounts of phenyldiacetatothallium, ammonium iodide, and aqueous ammonium hydroxide (58 wt. % $NH_4OH$) are charged to a 30 cc. glass insert which is closed at one end and which is provided at the other end with a dip tube capillary (about 1 mm. in diameter). The glass insert is then placed in a chilled 80 cc. steel container into which liquid ammonia is charged in those runs employing ammonia (Runs 5-7). The steel bomb is then sealed, attached to a rotating disk and placed in a constant temperature oil bath having a temperature of about 200° C. After twenty hours, the bomb is removed from the oil bath and allowed to cool to room temperature. The glass insert is then removed, weighed and sampled. The sample is analyzed using gas chromatography and the weight percent of iodobenzene and biphenyl and the combined weight percent of of aniline and phenol in the

EXAMPLE 3

Following the general procedure set forth in Example 2, indicated amounts of phenyl-diacetatothallium, promoter, ammonia, and either water, methanol, benzene or dimethyl formamide (DMF) as solvent are charged either to an open-capillary glass insert (Runs 1-9, Table 2A; Runs 1-7 and 9-10, Table 2B) placed in a steel reactor described in Example 2, or charged to a 75 cc. stainless steel reactor which is then sealed (Run 10, Table 2A; Run 8, Table 2B). In each run the reactor is attached to a rotating disk and heated in an oil bath having a temperature of 200° C. for a period of 20 hours, after which the reactor is cooled and the contents sampled and analyzed as indicated in Example 2 to determine the amounts of aniline, phenol, iodobenzene and biphenyl present, thereby giving the data set forth in Tables 2A and 2B. In Table 2A, Runs 1-9 report yields of aniline and phenol as combined yields; separate yields of aniline and phenol are given for Run 10. No products are analyzed for phenol in the runs of Table 2B (except Run 8).

TABLE 2A

| Run No. | CHARGE TO REACTOR - MILLIMOLES | | | | | PRODUCT YIELD - MOLE % | | |
|---|---|---|---|---|---|---|---|---|
| | Metal-late* | Promoter | | $NH_3$ | Solvent | | Aniline + Phenol | Phenyl Iodide | Biphenyl |
| 1 | 4.9 | $NH_4I$ | 11 | 294 | $H_2O$ | 444 | 16.4 | 3.7 | nil |
| 2 | " | $NH_4I$ | 5.6 | " | " | " | 5.1 | 1.2 | nil |
| 3 | " | $NH_4I$ | 11 | " | " | " | 9.2 | 2.4 | nil |
| 4 | " | $NH_4I$ | 5.6 | 412 | " | " | 21.5 | 0.8 | 0.3 |
| 5 | " | $NH_4I$ | " | 382 | " | " | 35.3 | 1.7 | 0.3 |
| 6 | " | $NH_4Br$ | 5.5 | 447 | " | " | 3.7 | — | 0.3 |
| 7 | " | $NH_4Cl$ | 5.4 | 465 | " | " | 0.7 | — | 0.6 |
| 8 | " | $NH_4F$ | 4.6 | 412 | " | " | 5.7 | — | 0.4 |
| 9 | " | $NH_4I$ | 2.8 | 441 | " | " | 3.5 | 1.3 | nil |
| 10 | " | $NH_4I$ | 5.6 | 429 | " | " | ** | 3.5 | nil |

* Phenyldiacetato thallium

TABLE 2A-continued

| Run No. | Metal-late* | Promoter | NH$_3$ | Solvent | Aniline + Phenol | Phenyl Iodide | Biphenyl |
|---|---|---|---|---|---|---|---|

CHARGE TO REACTOR - MILLIMOLES / PRODUCT YIELD - MOLE %

**  
| Run No. | Aniline | Phenol |
|---|---|---|
| 10 | 26.8 | 2.9 |

TABLE 2B

| Run No. | Metal-late* | Promoter | NH$_3$ | Solvent | | Aniline | Phenyl Iodide | Biphenyl |
|---|---|---|---|---|---|---|---|---|
| 1** | 5.6 | NH$_4$I | 5.6 | 329 | CH$_3$OH | 94 | 1.3 | 2.3 | nil |
| 2 | 4.9 | " | 1.4 | 328 | " | 198 | 4.4 | 2.5 | 0.3 |
| 3 | " | " | 5.6 | 429 | " | " | 3.5 | 13.8 | 0.4 |
| 4 | " | " | 11 | 312 | " | " | 1.8 | 43.0 | 0.3 |
| 5 | " | " | 11.2 | ≠ | " | " | nil | 47.3 | nil |
| 6 | " | " | 2.8 | 444 | Benzene | 90 | 9.2 | 2.9 | 1.6 |
| 7 | " | " | 5.6 | 390 | " | " | 27.6 | 4.1 | 0.9 |
| 8** | " | " | 11.2 | 435 | " | " | 1.2 | 39.2 | 0.25 |
| 9*** | 4.4 | " | 5.6 | — | DMF | 60 | 4.2 | 1.3 | nil |
| 10 | 4.9 | " | " | — | " | 103 | 6.3 | 9.5 | 0.3 |

*Phenyldiacetato thallium  
**Product in Run 8 also analyzed for phenol (none detected).  
***Charge to reactor includes NH$_4$OH (as 58 wt. % aqueous solution): Run 1-59.5 mmoles; Run 9-246 mmoles.  
≠ Ammonia is introduced in an amount sufficient to provide partial pressure of ammonia above the liquid of about 114 psig at room temperature.

In Run 7 of Table 2B, the described material from the gas chromatographic analysis is passed through a refrigerating device and material corresponding to the aniline peak is condensed, recovered and compared by infra red spectroscopy with a sample of pure aniline obtained from an independent source. The identification of the condensed material as aniline is verified.

The product mixture formed in Run 5 of Table 2B is also analyzed for phenol and anisole. No phenol is detected. Anisole content is found to comprise 0.4 weight percent of recovered product mixture, corresponding to a yield of about 3.5 mole % based on metallate charged. As will be apparent from the foregoing, the reaction of aromatic-thallium (III) metallate with sources of different nucleophiles in a reaction zone for nucleophillic substitution on the aromatic substrate of the metallate, occurs by way of competing reactions, so that the product mixture obtained will vary depending on relative reaction rates, nucleophile sources employed, relative concentration of nucleophile sources and reaction conditions.

EXAMPLE 4

Following the procedure of Example 2, selected amounts of phenyl diacetatothallium are reacted in an aqueous medium in either a glass lined reactor (sealed glass insert, Run 2) or in a 75 cc. stainless steel bomb (Runs 1 and 3-6) with either ammonia or an ammonium compound (NH$_4$I, NH$_4$Cl, NH$_4$Br, NH$_4$F or ammonium acetate). In Table 3 below the yield of aniline and phenol are reported as combined values.

TABLE 3

| Run No. | Metal-late* | Ammonia Source | | H$_2$O | Aniline | Phenol | Phenyl Iodide | Biphenyl |
|---|---|---|---|---|---|---|---|---|
| 1 | 4.9 | NH$_4$I | 4.9 | 440 | 0.36 | 25.1 | nil | nil |
| 2 | " | NH$_3$ | 453 | " | ** | ** | — | 0.4 |
| 3 | " | NH$_4$Cl | 4.9 | " | nil | 18.8 | — | nil |
| 4 | " | NH$_4$F | " | " | nil | trace | — | trace |
| 5 | " | NH$_4$Br | " | " | 0.11 | 17.8 | — | nil |
| 6 | " | NH$_4$OAc≠ | " | " | trace | 9.3 | — | 1.0 |

*Phenyldiacetato thallium  
**In Run 2, the yields of aniline and phenol are reported as combined yield = 3.3 mole %.  
≠ As used hereinafter, "OAc" is intended to refer to the acetate (i.e. "OOCCH$_3$") moiety.

EXAMPLE 5

Following the general procedure of Example 2, selected amounts of phenyldiacetato thallium, ammonium iodide, ammonia and water, together with the selected promoter, are charged to either a reactor as described in Example 2 (open capillary, steel reactor—Runs 1-9) or to a 75 cc. stainless steel reactor (Run 10), which is then sealed, attached to a rotating disk and placed in a constant temperature oil bath having a temperature of about 200° C. After 20 hours, the reactor is removed from the oil bath and allowed to cool to room temperature after which the contents are removed, weighed and sampled for analysis in accordance with the procedure described in Example 2. In Runs 1-9, summarized in Table 4, the quantity of aniline and phenol produced is reported as a combined yield. Separate yields of aniline and phenol are reported for Run 10.

TABLE 4

| Run No. | Metal-late* | NH₃ | Promoter | | NH₄I | H₂O | Aniline + Phenol | Phenyl Iodide | Biphenyl |
|---|---|---|---|---|---|---|---|---|---|
| | | | CHARGE TO REACTOR - MILLIMOLES | | | | PRODUCT YIELD - MOLE % | | |
| 1 | 4.9 | 458 | CuCl | 4.9 | 5.6 | 445 | 50.5 | nil | nil |
| 2** | " | 441 | " | " | " | " | 65.6 | nil | nil |
| 3 | " | 446 | " | " | 11.2 | " | 81.8 | nil | nil |
| 4 | 2.5 | 440 | CuCl₂ | " | 5.6 | 440 | 98.0 | nil | nil |
| 5 | 4.9 | 440 | " | " | " | " | 96.3 | nil | nil |
| 6 | " | 412 | " | " | 11.2 | " | 88.0 | nil | nil |
| 7 | " | 410 | " | 9.8 | 5.6 | " | 98.0 | nil | nil |
| 8 | 9.8 | 440 | " | " | " | " | 69.0 | nil | nil |
| 9 | 2.5 | 410 | 2FeI₂ . H₂O | 4.7 | " | " | 31.4 | 7.1 | nil |
| 10 | 4.9 | 412 | Cu Powder | 4.9 | 4.9 | " | *** | nil | 0.1 |

*Phenyldiacetato thallium
**6 Hour reaction time used in these runs
***Aniline = 13.9 mole %; Phenol = 26.6 mole %.

EXAMPLE 6

Following the procedure set forth in Example 2, selected amounts of phenyldiacetato thallium, ammonium iodide, ammonia and methanol are reacted in the presence of promoter and the product mixture analyzed as in Example 2. Data thereby obtained are set forth in Table 5 below.

TABLE 5

| Run No. | Metal-late* | NH₃ | Promoter | | NH₄I | CH₃OH | Aniline | Phenyl Iodide | Biphenyl |
|---|---|---|---|---|---|---|---|---|---|
| | | | CHARGE TO REACTOR - MILLIMOLES | | | | PRODUCT YIELD - MOLE % | | |
| 1 | 4.9 | 398 | CuCl | 4.9 | 11.2 | 198 | 49.5 | 2.1 | 0.6 |
| 2 | " | 440 | FeI₂ . 4H₂O | 4.7 | 5.6 | " | 32.2 | 63.7 | 0.7 |
| 3** | " | 410 | CuCl₂ | 4.9 | 11.2 | " | 78.6 | nil | 0.3 |
| 4 | " | — | FeI₂ . H₂O | " | — | " | nil | 16.7 | nil |
| 5 | 9.0 | 435 | CuCl₂ | " | 9.3 | " | 34 | nil | nil |

*Phenyldiacetato thallium
**6 Hour reaction time used in this run.
Note:
Runs 1-4: open capillary, steel reactor, as described in Example 2. Run 5: 75 cc. stainless steel reactor.

EXAMPLE 7

Following the procedure set forth in Example 2, selected amounts of phenyldiacetato thallium, ammonia, benzene and ammonium iodide are reacted in the presence of promoter and the product analyzed. Data thereby obtained are set forth in Table 6 below.

TABLE 6

| Run No. | Metal-late* | NH₃ | Promoter | | NH₄I | Benzene | Aniline | Phenyl Iodide | Biphenyl |
|---|---|---|---|---|---|---|---|---|---|
| | | | CHARGE TO REACTOR - MILLIMOLES | | | | PRODUCT YIELD - MOLE % | | |
| 1 | 4.9 | 420 | CuCl₂ | 4.9 | 11.0 | 90 | 64.7 | nil | nil |
| 2 | " | 447 | CuCl | " | 5.6 | " | 43.1 | nil | 0.8 |

*Phenyldiacetato thallium
Note:
Run 1: open capillary, steel reactor, as in Example 2.
Run 2: 75 cc. stainless steel reactor.

EXAMPLE 8

Following the procedure set forth in Example 2, selected amounts of phenyldiacetato thallium, ammonia and water are reacted in the presence of promoter. In the runs summarized in Table 7 A, the quantity of phenol and aniline produced is reported as a combined yield. Separate yields of aniline and phenol are given in Table 7 B for the runs summarized therein.

TABLE 7 A

| Run No. | Metallate* | NH₃ | Promoter | | H₂O | Aniline + Phenol | Phenyl Iodide | Biphenyl |
|---|---|---|---|---|---|---|---|---|
| | | CHARGE TO- MILLIMOLES | | | | PRODUCT YIELD - MOLE % | | |
| 1 | 4.9 | 440 | CuCl | 4.9 | 440 | 63.6 | — | nil |
| 2 | " | 430 | ZnI₂ | " | " | 38.4 | 0.3 | 1.0 |
| 3 | " | 400 | CuCr₂ | " | " | 53.8 | — | nil |
| 4 | " | 460 | CuF₂ | " | " | 77.6 | — | nil |
| 5 | " | 380 | CuI | " | " | 73.0 | 0.8 | nil |
| 6 | " | " | BiI₃ | " | " | 35.0 | 1.9 | nil |
| 7 | " | 465 | CoI₂ | " | " | 41.9 | nil | 0.4 |
| 8 | " | 450 | CrCl₃ | " | " | 2.4 | — | 0.9 |
| 9 | " | 460 | AgI | " | " | 14.7 | nil | 0.9 |
| 10 | " | 465 | NiI₂ . 6H₂O | " | " | 43.7 | nil | 0.1 |

TABLE 7 A-continued

| Run No. | CHARGE TO- MILLIMOLES | | | | PRODUCT YIELD - MOLE % | | |
|---|---|---|---|---|---|---|---|
| | Metallate* | NH₃ | Promoter | | H₂O | Aniline + Phenol | Phenyl Iodide | Biphenyl |
| 11 | " | 380 | CdI₂ | " | " | 52.4 | nil | 0.2 |
| 12 | " | 390 | PdCl₂ | " | " | 1.5 | — | 1.0 |
| 13 | 9.8 | 390 | CuCl₂ | 20.0 | " | 58.4 | — | nil |
| 14 | 4.9 | 440 | Cu(OAc)₂ . H₂O | 9.8 | " | 46.0 | — | nil |
| 15 | 4.9 | 400 | Fe(OAc)₂ . H₂O | 4.9 | 440 | 2.2 | | 0.3 |
| 16 | " | 380 | CuCl | " | " | 47.2 | | 0.1 |
| 17 | 2.5 | 380 | Cu(OAc)₂ . H₂O | 2.5 | " | 20.0 | | nil |
| 18 | 4.9 | " | Cu(OAc)₂ . H₂O | 4.9 | " | 31.0 | | nil |
| 19 | " | 442 | LiI | 4.9 | 444 | ** | | 0.1 |
| 20 | " | 412 | CuI | " | " | ** | | nil |

*Phenyldiacetato thallium

**     Yield - Mole %

| Run No. | (Aniline) | (Phenol) |
|---|---|---|
| 19 | 24.1 | 15.6 |
| 20 | 18.9 | 51.6 |

Note:
Runs 1-17: open capillary, steel reactor, as in Example 2.
Runs 18-20: 75 cc. stainless steel reactor.

TABLE 7 B

| Run No. | CHARGE TO REACTOR - MILLIMOLES | | | | | PRODUCT YIELD - MOLE % | | | |
|---|---|---|---|---|---|---|---|---|---|
| | Metallate* | NH₃ | Promoter | | H₂O | Aniline | Phenol | Phenyl Iodide | Biphenyl |
| 1 | 4.9 | 453 | CuI | 4.9 | 440 | 38.4 | 55.7 | nil | nil |
| 2 | " | 446 | CuCl₂ | " | " | 15.0 | 39.3 | — | 0.14 |
| 3≠ | " | 442 | " | " | " | 22.2 | 30.0 | — | 0.3 |
| 4 | " | 406 | CuF₂ | " | " | 33.5 | 30.4 | — | <0.1 |
| 5 | " | 400 | Cu*** | " | " | 14.1 | 21.1 | — | 0.09 |
| 6 | " | 447 | Cu(OAc)₂ | " | " | 30.1 | 27.0 | — | 0.1 |
| 7 | " | ** | " | " | " | 17.9 | 33.6 | — | trace |

*Phenyldiacetato thallium
**13.49 grams of aqueous ammonium hydroxide solution (58%).
***Finely divided (powdered) metallic copper.
≠ Gas chromatographic analysis gives additional peak believed to comprise phenyl acetate (0.6 mole % yield).

Note:
Run 4: Open capillary, steel reactor, as in Example 2.
Runs 1-3 and 5-7: 75 cc. stainless steel reactor.

EXAMPLE 9

Following the procedure set forth in Example 2 above, selected amounts of phenyl-diacetato thallium, ammonia, and the selected solvent are reacted in the presence of a promoter with the data thereby obtained being set forth in Table 8.

EXAMPLE 10

Following the procedure set forth in Example 2, selected amounts of phenyldiacetato thallium, ammonium iodide and solvent are reacted in the presence of a promoter, with the data thereby obtained being set forth in Table 9.

TABLE 8

| Run No. | CHARGE TO REACTOR - MILLIMOLES | | | | | | PRODUCT YIELD - MOLE % | | |
|---|---|---|---|---|---|---|---|---|---|
| | Metallate* | NH₃ | Promoter | | Solvent | | Aniline | Phenyl Iodide | Biphenyl |
| 1 | 4.9 | 460 | I₂ | 4.9 | CH₃OH | 198 | 11.0 | 65.3 | nil |
| 2 | " | 394 | Cu(OAc)₂ . H₂O | " | " | " | 30.5 | — | nil |
| 3 | " | 430 | " | " | Benzene | 90 | 51.3 | — | nil |
| 4 | " | 424 | CuI | " | CH₃OH | 198 | 37.1 | nil | nil |
| 5 | " | 465 | CuCl₂ | " | " | " | 26.5 | — | nil |
| 6 | " | 435 | " | " | Benzene | 90 | 39.0 | — | 1.2 |
| 7 | " | 465 | CuF₂ | " | " | " | 29.9 | — | nil |

*Phenyldiacetato thallium

Note:
Runs 1, and 3: open capillary, steel reactor, as in Example 2.
Runs 2 and 4-7: 75 cc. stainless steel reactor.

TABLE 9

| Run No. | CHARGE TO REACTOR - MILLIMOLES | | | | | PRODUCT YIELD - MOLE % | | |
|---|---|---|---|---|---|---|---|---|
| | Metal-late* | Promoter | | NH₄I | Solvent | | Aniline | Phenyl Iodide | Biphenyl |
| 1 | 4.9 | CuCl₂ | 4.9 | 5.6 | Benzene | 90 | 3.5 | 27.6 | 0.3 |
| 2 | " | " | " | " | H₂O | 444 | 14.3 | nil | nil |
| 3** | " | " | " | " | CH₃OH | 198 | nil | nil | nil |

*Phenyldiacetato thallium
**Product mixture is also found to contain about 0.02 weight percent anisole (about 0.5 mole % yield) and about 5.2 weight percent chlorobenzene (about 50 mole % yield). Value represents combined yield of phenol and aniline.
Note:
All Runs: open capillary, steel reactor, as in Example 2.

EXAMPLE 11

Following the general procedure of Example 2, 4.9 mmoles of phenyldiacetato thallium and 444 mmoles of water are charged to a 75 cc stainless steel reactor which is first washed successively with two 50 cc portions of concentrated nitric acid, followed by successive washings with distilled water and acetone, and blown dry with nitrogen. The reactor is then sealed, attached to a rotating disk and placed in a constant temperature oil bath having a temperature of about 200° C. for a period of about 20 hours. At the end of this time, the steel reactor is removed from the oil bath and allowed to cool to room temperature, after which the contents are removed and analyzed, and are found to contain phenol in a yield of about 0.7 mole percent, based on the moles of metallate charged to the reactor. The product mixture is also found to contain about 10 mole percent biphenyl.

EXAMPLE 12

Following the general procedure of Example 2, 1.95 grams (4.9 mmoles) of phenyl-diacetato thallium, 0.98 gram (4.9 mmoles) of Cu(OAc)₂.H₂O as promoter, and 8.0 grams (444 mmoles) of water as nucleophile source are placed in a 75 cc stainless steel reactor which is then sealed, attached to a rotating disk and placed in a constant temperature oil bath having a temperature of about 200° C. for a period of about 20 hours. At the end of this time, the steel reactor is removed from the oil bath and followed to cool to room temperature, after which the contents are removed and found to weight 8.80 grams, which on subsequent gas chromatographic analysis is found to contain about 2.01 weight percent phenol, which corresponds to a phenol yield of about 30.0 mole percent, based on the moles of metallate charged to the reactor. No biphenyl is detected in the product mixture.

On desorption, the desorbed material from the gas chromatographic analysis is passed through a refrigerating device and material corresponding to the phenol peak is condensed, recovered and compared by infrared spectroscopy with a sample of pure phenol obtained from an independent source. The identification of the condensed material as phenol is verified.

EXAMPLE 13

The general procedure of Example 12 is repeated employing 4.9 mmoles of cuprous iodide (CuI) as promoter in the place of the cupric acetate employed in Example 12. At the end of the reaction time, the product mixture is found to contain phenol in an amount which provides a 52 mole percent yield of phenol, based on the moles of metallate charged to the reactor. No biphenyl or phenyl iodide is detected in the product mixture.

EXAMPLE 14

A selected amount of anhydrous thallic tris-trifluoroacetate is slowly added to a stirred vessel containing about a 20-fold molar excess of benzene, and the mixture so formed is heated to a temperature of 120° C. at autogenous pressure and is allowed to react for 20 hours. The material is then recovered from the procedure set forth in Example 1.

Employing the procedure set forth in Example 2 above (and the reactor there described), selected amounts of phenyl bis(-trifluoroacetato) thallium are reacted in a series of runs with ammonia in the presence of either cupric acetate or cupric chloride as promoter and in the presence of either methanol or benzene as solvent. The selected promoter and the metallate are employed in each run in approximately equimolar amounts, and ammonia is employed in approximately a 100-fold molar excess, based on the moles of metallate charged to the reactor. The product mixture in each run is analyzed and is found to contain aniline in a yield of from about 30 to 50 mole percent, based on the moles of metallate charged to the reactor. No biphenyl is detected in the product mixture.

EXAMPLE 15

A selected amount of anhydrous thallic triisobutyrate is slowly added to a stirred vessel containing about 20-fold molar excess of benzene, and the mixture so formed is heated to a temperature of 120° C. at autogenous pressure and is allowed to react for 20 hours. The material is then recovered from the reaction mixture and identified as phenyl-diisobutyrato-thallium following the procedure set forth in Example 1.

Employing the procedure set forth in Example 2 above (and the reactor there described), selected amounts of phenyl-diisobutyrato-thallium are reacted in a series of runs with ammonia in the presence of either cupric acetate or cupric chloride as promoter and in the presence of either methanol or benzene as solvent. The selected promoter and the metallate are employed in each run in approximately equimolar amounts, and ammonia is employed in approximately a 100-fold molar excess, based on the moles of metallate charged to the reactor. The product mixture in each run is analyzed and is found to contain aniline in a yield of from about 30 to 50 mole percent, based on the moles of metallate charged to the reactor. No biphenyl is detected in the product mixture.

EXAMPLE 16

A selected amount of anhydrous thallic tris-p-toluenesulfonate is slowly added to a stirred vessel containing about a 20-fold molar excess of benzene, and the mixture so formed is heated to a temperature of 120° C. at autogenous pressure and is allowed to react for 20 hours. The material is then recovered from the reaction mixture and identified as phenyl-bis-p-toluenesulfonato-thallium following the procedure set forth in Example 1.

Employing the procedure set forth in Example 2 above (and the reactor there described), selected amounts of phenyl-bis-p-toluenesulfonato-thallium are reacted in a series of runs with ammonia in the presence of either cupric acetate or cupric chloride as promoter and in the presence of either methanol or benzene as solvent. The selected promoter and the metallate are employed in each run in approximately equimolar amounts, and ammonia is employed in approximately a 100-fold molar excess, based on the moles of metallate charged to the reactor. The product mixture in each run is analyzed and is found to contain aniline in a yield of from about 40 to 60 mole percent, based on the moles of metallate charged to the reactor. No biphenyl is detected in the product mixture.

EXAMPLE 17

A selected amount of anhydrous thallic sulfate is slowly added to a stirred vessel containing about a 20-fold molar excess of benzene, and the mixture so formed is heated to a temperature of 120° C. at autogenous pressure and is allowed to react for 20 hours. The material is then recovered from the reaction mixture and identified as phenyl-sulfato-thallium following the procedure set forth in Example 1.

Employing the procedure set forth in Example 2 above (and the reactor there described), selected amounts of phenyl-sulfato-thallium are reacted in a series of runs with ammonia in the presence of either cupric acetate or cupric chloride as promoter and in the presence of either methanol or benzene as solvent. The selected promoter and the metallate are employed in each run in approximately equimolar amounts, and ammonia is employed in approximately 100-fold molar excess, based on the moles of metallate charged to the reactor. The product mixture in each run is analyzed and is found to contain aniline in a yield of from about 15 to 30 mole percent, based on the moles of metallate charged to the reactor. No biphenyl is detected in the product mixture.

EXAMPLE 18

A selected amount of anhydrous thallic nitrate is slowly added to a stirred vessel containing about a 20-fold molar excess of benzene, and the mixture so formed is heated to a temperature of 120° C. at autogenous pressure and is allowed to react for 20 hours. The material is then recovered from the reaction mixture and identified as phenyl-dinitrato-thallium following the procedure set forth in Example 1.

Employing the procedure set forth in Example 2 above (and the reactor there described), selected amounts of phenyl-dinitrato-thallium are reacted in a series of runs with ammonia in the presence of either cupric acetate or cupric chloride as promoter and in the presence of either methanol or benzene as solvent. The selected promoter and the metallate are employed in each run in approximately equimolar amounts, and ammonia is employed in approximately a 100-fold molar excess, based on the moles of metallate charged to the reactor. The product mixture in each run is analyzed and is found to contain aniline in a yield of from about 20 to 30 mole percent, based on the moles of metallate charged to the reactor. No biphenyl is detected in the product mixture.

EXAMPLE 19

A selected amount of anhydrous thallic chloride is slowly added to a stirred vessel containing about a 20-fold molar excess of benzene, and the mixture so formed is heated to a temperature of 120° C. at autogenous pressure and is allowed to react for 20 hours. The material is then recovered from the reaction mixture and identified as phenyl-dichloro-thallium following the procedure set forth in Example 1.

Employing the procedure set forth in Example 2 above (and the reactor there described), selected amounts of phenyl-dichloro-thallium are reacted in a series of runs with ammonia in the presence of either cupric acetate or cupric chloride as promoter and in the presence of either methanol or benzene as solvent. The selected promoter and the metallate are employed in each run in approximately equimolar amounts, and ammonia is employed in approximately a 100-fold molar excess, based on the moles of metallate charged to the reactor. The product mixture in each run is analyzed and is found to contain aniline in a yield of from about 10 to 30 mole percent, based on the moles of metallate charged to the reactor. No biphenyl is detected in the product mixture.

EXAMPLE 20

A selected amount of anhydrous thallic acetate is slowly added to a stirred vessel containing about a 20-fold molar excess of toluene, and the mixture so formed is heated to a temperaure of 120° at autogenous pressure and is allowed to react for 20 hours. The material is then recovered from the reaction mixture and identified as p-tolyl-diacetato-thallium following the procedure set forth in Example 1.

Employing the procedure set forth in Example 2 above (and the reactor there described), selected amounts of p-tolyl-diacetato-thallium are reacted in a series of runs with ammonia in the presence of either cupric acetate or cupric chloride as promoter and in the presence of either methanol or toluene as solvent. The selected promoter and the metallate are employed in each run in approximately equimolar amounts and ammonia is employed in approximately a 100-fold molar excess, based on the moles of metallate charged to the reactor. The product mixture in each run in analyzed and is found to contain p-toluidine in a yield of from about 20 to 50 mole percent, based on the moles of metallate charged to the reactor. No bitolyl is detected in the product mixture.

EXAMPLE 21

A selected amount of anhydrous thallic acetate is slowly added to a stirred vessel containing about a 20-fold molar excess of ethyl-benzene, and the mixture so formed is heated to a temperature of 120° C. at autogenous pressure and is allowed to react for 20 hours. The material is then recovered from the reaction mixture and identified as p-ethylphenyl-diacetato-thallium following the procedure set forth in Example 1.

Employing the procedure set forth in Example 2 above (and the reactor there described), selected amounts of p-ethylphenyl-diacetato-thallium are reacted in a series of runs with ammonia in the presence of either cupric acetate or cupric chloride as promoter and in the presence of either methanol or ethyl benzene as solvent. The selected promoter and the metallate are employed in each run in approximately equimolar amounts and ammonia is employed in approximately a 100-fold molar excess, based on the moles of metallate charged to the reactor. The product mixture in each run is analyzed and is found to contain p-ethyl aniline in a yield of from about 30 to 50 mole percent, based on the moles of metallate charged to the reactor. No 4,4'-diethyl-biphenyl is detected in the product mixture.

It will be obvious that various changes and modifications may be made without departing from the invention and it is intended, therefore, that all matter contained in the foregoing description shall be interpreted as illustrative only and not limitative of the invention.

I claim:

1. A process for the preparation of a nucleophilically ring-substituted aromatic compound, wherein the nucleophilic substituent comprises hydroxy, which comprises reacting, in a liquid medium at a temperature of from about 20° to 500° C., a source of the hydroxy nucleophilic substituent with an aromatic thallium (III) metallate comprising an aromatic compound containing at least one aromatic ring on which is substituted a thallic group having the formula

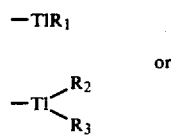

wherein $R_1$ is $-CO_3$ or $-SO_4$, and $R_2$ and $R_3$ are the same or different and are selected from the group consisting of

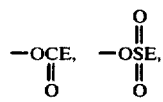

$-NO_3$ and halide, wherein E is a member selected from the group consisting of alkyl of from 1 to 12 carbon atoms, cycloalkyl of from 3 to 12 carbon atoms, alkaryl and aralkyl of from 7 to 20 carbon atoms, mononuclear aryl of 6 to 12 carbon atoms, derivatives of the above hydrocarbyl groups wherein at least one carbon atom is replaced by oxygen, derivatives of the above hydrocarbyl and oxygen-substituted hydrocarbyl groups in which at least one hydrogen atom is replaced by a member selected from the group consisting of $-NO_2$, $-OH$, and alkoxy of from 1 to 6 carbon atoms, and halogenated derivatives of the foregoing, said aromatic compound comprising a member selected from the group consisting of compounds of the formula

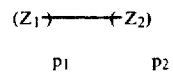

wherein $p_1$ is an integer of 1 to 3; $p_2$ is an integer of 0 to 3; $Z_1$ is a radical selected from the group consisting of phenyl, naphthyl, anthryl, phenanthryl, furyl, indenyl, isoindenyl, benzofuryl, and tetrahydrofuryl; and $Z_2$ is a radical selected from the group consisting of monovalent alkyl of from 1 to 6 carbon atoms, monovalent cycloalkyl of from 3 to 10 carbon atoms, nitro, hydroxy, phenyl, alkyl-substituted phenyl having a total of from 7 to 12 carbon atoms, alkoxy of from 1 to 6 carbon atoms, alkoxy-substituted alkyl of from 2 to 7 carbon atoms, aryloxy of from 6 to 12 carbon atoms, aralkyl of from 7 to 12 carbon atoms, saturated aliphatic carboxyl of from 1 to 8 carbon atoms, aryl carboxyl of from 8 to 12 carbon atoms, hydroxy-substituted alkyl of from 1 to 6 carbon atoms, alkyl esters of from 2 to 8 carbon atoms, divalent alkyl of from 1 to 12 carbon atoms, halogenated derivatives of the foregoing and halogen, with the proviso that when $Z_2$ is divalent alkyl, $p_1$ is 2 and $p_2$ is 1, to form said nucleophilically ring-substituted aromatic compound, said source of hydroxy nucleophile comprising a member selected from the group consisting of water, alkali metal hydroxide, alkaline earth metal hydroxide, ammonium hydroxide, quaternary ammonium hydroxide, and mixtures thereof.

2. The process of claim 1 wherein said organic aromatic compound is a member selected from the group consisting of benzene, naphthalene, anthracene, phenanthracene, furan, indene, isoindene, benzofuan and tetrahydrofuran.

3. The process of claim 1 wherein said thallic group comprises a member of the group consisting of moieties of the formula

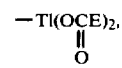

wherein E is as defined in claim 1.

4. The process of claim 1 wherein said aromatic-thallium (III) metallate and said nucleophile source are reacted in the presence of a promoter.

5. The process of claim 4 wherein said promoter comprises a member selected from the group consisting of iodine sources, copper sources and mixtures thereof.

6. The process of claim 5 wherein the iodine source comprises at least one inorganic salt containing iodine combined with a member selected from the group consisting of H, $NH_4^+$, cations dervied from Bi, Cu, Fe, Co, Zn, Ni, Pd, Ag, Cd, Na, K or Li, and mixtures thereof.

7. The process of claim 5 wherein the copper source comprises at least one member selected from the group consisting of the carbonates, oxides, hydroxides, nitrates, halides, lower alkoxides, phenoxides, and carboxylates of copper.

8. The process of claim 5 wherein the promoter is selected from the group consisting of cuprous and cupric acetates and iodides.

9. The process of claim 1 wherein said nucleophilically ring-substituted aromatic compound which is formed is recovered from the liquid reaction medium containing the same.

10. The process according to claim 1 wherein said aromatic compound comprises benzene.

11. The process according to claim 1 wherein said nucleophilically ring-substituted aromatic compound comprises phenol.

12. The process according to claim 5 wherein the promoter is employed in the liquid medium in an amount of at least $1 \times 10^{-4}$ weight percent, calculated as contained iodine or copper.

13. The process according to claim 1 wherein said temperature is from about 50° to 300° C.

14. The process according to claim 7 wherein the promoter is employed in the liquid reaction medium in an amount of from about 10 to 50,000 ppm, based on the copper content of the promoter.

15. A process for the preparation of phenol which comprises reacting, in a liquid medium at a temperature of from about 50° to 300° C., a source of hydroxy nucleophile with a benzene thallium (III) metallate of the formula

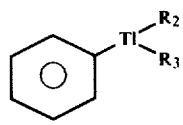

wherein $R_2$ and $R_3$ are the same or different and are selected from the group consisting of

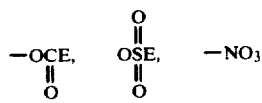

—$NO_3$ and halide, wherein E is a member selected from the group consisting of alkyl of from 1 to 12 carbon atoms, cycloalkyl of from 3 to 12 carbon atoms, alkaryl and aralkyl of from 7 to 20 carbon atoms, mononuclear aryl of 6 to 12 carbon atoms, derivatives of the above hydrocarbyl groups wherein at least one carbon atom is replaced by oxygen, derivatives of the above hydrocarbyl and oxygen-substituted hydrocarbyl groups in which at least one hydrogen atom is replaced by a member selected from the group consisting of —$NO_2$, —OH and alkoxy of from 1 to 6 carbon atoms, and halogenated derivatives of the foregoing, said reaction being conducted in the presence of an effective amount of a promoter selected from the group consisting of sources of iodine, copper and mixtures thereof, said source of hydroxy nucleophile comprising a member selected from the group consisting of water, alkali metal hydroxide, alkaline earth metal hydroxide, ammonium hydroxide, quaternary ammonium hydroxide, and mixtures thereof, and recovering the phenol from the liquid medium.

16. The process according to claim 15 wherein said reaction is effected at a pressure of from 0.1 to 2000 atmospheres guage and for a time of from 0.1 to 100 hours, and said promoter is present in the liquid medium in an amount of at least about $1 \times 10^{-4}$ weight percent and comprises at least one member selected from the group consisting of elemental copper; elemental iodine; inorganic salts containing iodine combined with H, $NH_4^+$, cations derived from Bi, Cu, Fe, Co, Zn, Ni, Pd, Ag, Cd, Na, K or Li; and carbonates, oxides, hydroxides, nitrates, halides, lower alkoxides, phenoxides, and carboxylates of copper.

* * * * *